(12) United States Patent
Sharonov et al.

(10) Patent No.: US 9,113,822 B2
(45) Date of Patent: Aug. 25, 2015

(54) COLLIMATED BEAM METROLOGY SYSTEMS FOR IN-SITU SURGICAL APPLICATIONS

(71) Applicant: Covidien LP, Mansfield, MA (US)

(72) Inventors: Alexey Sharonov, Bethany, CT (US); Candido Dionisio Pinto, Pacifica, CA (US)

(73) Assignee: Covidien LP, Mansfield, MA (US)

( * ) Notice: Subject to any disclaimer, the term of this patent is extended or adjusted under 35 U.S.C. 154(b) by 292 days.

(21) Appl. No.: 13/650,156

(22) Filed: Oct. 12, 2012

(65) Prior Publication Data

US 2013/0110006 A1 May 2, 2013

Related U.S. Application Data

(60) Provisional application No. 61/551,960, filed on Oct. 27, 2011.

(51) Int. Cl.
| | | |
|---|---|---|
| *A61B 5/107* | (2006.01) | |
| *A61B 1/00* | (2006.01) | |
| *A61B 19/00* | (2006.01) | |
| *A61B 17/34* | (2006.01) | |

(52) U.S. Cl.
CPC ........... *A61B 5/1076* (2013.01); *A61B 1/00131* (2013.01); *A61B 5/1079* (2013.01); *A61B 19/46* (2013.01); *A61B 17/3423* (2013.01); *A61B 2019/461* (2013.01); *A61B 2019/521* (2013.01)

(58) Field of Classification Search
CPC ........ G01B 11/24; G01B 11/26; G01B 11/27; G01C 3/00; G01C 5/00; G01C 15/00; A61B 18/18; A61B 5/00; A61B 5/107
USPC ............................................ 33/227, 511, 512
See application file for complete search history.

(56) References Cited

U.S. PATENT DOCUMENTS

| | | | |
|---|---|---|---|
| 3,817,635 | A | 6/1974 | Kawahara |
| 3,819,267 | A | 6/1974 | Kawahara |
| 3,943,361 | A | 3/1976 | Miller |
| 4,281,931 | A | 8/1981 | Chikama |

(Continued)

FOREIGN PATENT DOCUMENTS

| | | |
|---|---|---|
| DE | 3629435 A1 | 3/1987 |
| DE | 10 2010 025752 | 1/2012 |

(Continued)

OTHER PUBLICATIONS

European Search Report from EP 12190094.8 dated Mar. 4, 2013 (6 pgs.).

(Continued)

*Primary Examiner* — Yaritza Guadalupe-McCall

(57) ABSTRACT

A metrology system includes a collinear array of uniformly spaced light elements for propagating parallel light beams. The parallel light beams assist in producing a light pattern on a target site. A method of measuring a dimension of a target site includes the steps of projecting uniformly spaced parallel light beams to form a light pattern having uniformly spaced elements on the target site, aligning the light pattern such that a maximum number of the uniformly spaced elements is positioned along the dimension; and counting the maximum number of the uniformly spaced elements positioned along the dimension.

17 Claims, 3 Drawing Sheets

(56) References Cited

U.S. PATENT DOCUMENTS

| | | | |
|---|---|---|---|
| 4,606,127 A * | 8/1986 | Task et al. ............... 33/1 G |
| 4,660,982 A | 4/1987 | Okada |
| 4,702,229 A | 10/1987 | Zobel |
| 4,834,070 A * | 5/1989 | Saitou ................ 600/108 |
| 4,902,123 A | 2/1990 | Yoder, Jr. |
| 4,958,932 A | 9/1990 | Kegelman et al. |
| 4,980,763 A | 12/1990 | Lia |
| 4,986,262 A | 1/1991 | Saito |
| 5,090,400 A | 2/1992 | Saito |
| 5,285,785 A | 2/1994 | Meyer |
| 5,558,666 A | 9/1996 | Dewey et al. |
| 5,669,871 A | 9/1997 | Sakiyama |
| 5,808,813 A | 9/1998 | Lucey et al. |
| 5,872,657 A * | 2/1999 | Rando ..................... 33/290 |
| 6,063,023 A | 5/2000 | Sakiyama et al. |
| 6,070,583 A | 6/2000 | Perelman et al. |
| 6,317,980 B2 * | 11/2001 | Buck, III ............ 33/DIG. 21 |
| 6,360,012 B1 | 3/2002 | Kreuzer |
| 6,377,353 B1 * | 4/2002 | Ellis ........................ 356/603 |
| 6,451,010 B1 | 9/2002 | Angeley |
| 6,482,148 B1 | 11/2002 | Luke |
| 6,508,761 B1 | 1/2003 | Ramsbottom et al. |
| 6,542,763 B1 | 4/2003 | Yamashita et al. |
| 6,611,698 B1 | 8/2003 | Yamashita et al. |
| 6,741,338 B2 | 5/2004 | McArthur et al. |
| 6,877,236 B1 * | 4/2005 | Williams ..................... 33/286 |
| 6,945,930 B2 | 9/2005 | Yokota |
| 7,003,890 B2 * | 2/2006 | Kavounas ..................... 33/286 |
| 7,090,670 B2 * | 8/2006 | Sink ................................ 606/9 |
| 7,310,431 B2 | 12/2007 | Gokturk et al. |
| 7,464,478 B2 * | 12/2008 | Adrian ........................ 33/286 |
| 7,486,805 B2 | 2/2009 | Krattiger |
| 7,532,311 B2 | 5/2009 | Henderson et al. |
| 7,556,599 B2 | 7/2009 | Rovegno |
| 7,720,532 B2 | 5/2010 | Hashimshony et al. |
| 7,812,968 B2 | 10/2010 | Bendall et al. |
| 7,862,555 B2 | 1/2011 | Chan et al. |
| 7,866,052 B2 * | 1/2011 | Schulze ...................... 33/1 G |
| 8,780,362 B2 * | 7/2014 | Sharonov et al. ............ 356/625 |
| 2005/0085717 A1 | 4/2005 | Shahidi |
| 2005/0090749 A1 | 4/2005 | Rubbert |
| 2005/0124988 A1 | 6/2005 | Terrill-Grisoni |
| 2005/0237423 A1 | 10/2005 | Nilson et al. |
| 2006/0092418 A1 | 5/2006 | Xu et al. |
| 2007/0229668 A1 * | 10/2007 | He et al. ..................... 348/195 |
| 2008/0024793 A1 | 1/2008 | Gladnick |
| 2008/0068197 A1 | 3/2008 | Neubauer et al. |
| 2008/0200808 A1 | 8/2008 | Leidel et al. |
| 2008/0221446 A1 | 9/2008 | Washburn et al. |
| 2009/0002485 A1 | 1/2009 | Fujiwara |
| 2009/0054767 A1 | 2/2009 | Telischak et al. |
| 2009/0270682 A1 | 10/2009 | Visser |
| 2010/0020333 A1 | 1/2010 | Kunz et al. |
| 2010/0046004 A1 | 2/2010 | Lee et al. |
| 2010/0201796 A1 | 8/2010 | Chan |
| 2011/0054308 A1 | 3/2011 | Cohen et al. |
| 2011/0279670 A1 | 11/2011 | Park |
| 2012/0101370 A1 | 4/2012 | Razzaque et al. |
| 2012/0229621 A1 * | 9/2012 | Turner et al. .................. 348/135 |
| 2013/0110005 A1 * | 5/2013 | Sharonov ..................... 600/587 |
| 2013/0110006 A1 * | 5/2013 | Sharonov et al. ............. 600/587 |
| 2013/0226037 A1 * | 8/2013 | Pinto et al. .................... 600/587 |
| 2013/0296712 A1 * | 11/2013 | Durvasula ..................... 600/477 |
| 2014/0031665 A1 * | 1/2014 | Pinto et al. .................... 600/407 |
| 2014/0202013 A1 * | 7/2014 | Smith ............................ 33/286 |
| 2014/0276097 A1 * | 9/2014 | Sharonov ..................... 600/476 |
| 2015/0051008 A1 * | 2/2015 | Schmok ....................... 473/220 |

FOREIGN PATENT DOCUMENTS

| | | |
|---|---|---|
| EP | 0403399 A2 | 12/1990 |
| EP | 1480067 A1 | 11/2004 |
| EP | 2106748 A1 | 10/2009 |
| EP | 2 524 650 A2 | 11/2012 |
| JP | 2011 185767 | 9/2011 |
| WO | WO 00/08415 A1 | 2/2000 |
| WO | WO 2005/013814 A1 | 2/2005 |

OTHER PUBLICATIONS

European Search Report from EP 12168466.6 dated Mar. 26, 2013 (10 pgs.).

European Search Report from EP 13156689.5 dated Apr. 26, 2013 (7 pgs.).

Extended European Search Report dated Jun. 12, 2014 for EP 14 15 8762.

European Search Report for EP Application No. 13156676.2-1553 dated Jul. 2, 2013. (7 pages).

European Search Report for EP Application No. 12190097.1 dated Sep. 16, 2013. (6 pgs.).

European Search Report for EP Application No. 13172563.2 dated Oct. 1, 2013. (8 pgs.).

European Search Report, Application No. EP 13 17 7731 dated Mar. 24, 2014.

European Search Report dated Nov. 28, 2013 in European Appln. No. 13 17 7731.

* cited by examiner

COLLIMATED BEAM METROLOGY SYSTEMS FOR IN-SITU SURGICAL APPLICATIONS

CROSS REFERENCE TO RELATED APPLICATION

The present application claims the benefit of and priority to U.S. Provisional Application Ser. No. 61/551,960, filed on Oct. 27, 2011, the entire contents of which are incorporated herein by reference.

BACKGROUND

1. Technical Field

The present disclosure relates to a method for measuring a dimension of a target site. More particularly, the present disclosure relates to a method of projecting a pattern of known size onto a target site for measuring the target site.

2. Background of the Related Art

Minimally invasive surgery, e.g., laparoscopic, endoscopic, and thoroscopic surgery, has many advantages over traditional open surgeries. In particular, minimally invasive surgery eliminates the need for a large incision, thereby reducing discomfort, recovery time, and many of the deleterious side effects associated with traditional open surgery.

The minimally invasive surgeries are performed through small openings in a patient's skin. These openings may be incisions in the skin or may be naturally occurring body orifices (e.g., mouth, anus, or vagina). In general, insufflation gas is used to enlarge the area surrounding the target surgical site to create a larger, more accessible work area.

During minimally invasive procedures, it is often difficult for a surgeon to determine sizes of various organs, tissues, and other structures in a surgical site. Various in-situ surgical metrology methods exist for measurement in a surgical site. Such methods require many moving parts and project images that change size and/or focus quickly as projectors move in or out of a surface of projection. A continuing need exists for in-situ surgical metrology methods that operate with a stable focus and no moving parts.

SUMMARY

A metrology system includes a collinear array of uniformly spaced light elements for propagating parallel light beams. The parallel light beams assist in producing a light pattern on a target site. The light elements may be attached to an endoscope or be a standalone device. The light pattern may include uniformly spaced collinear dots. A light pattern generating optics, such as diffractive optical elements, may produce a two-dimensional light pattern from the parallel light beams. The two-dimensional light pattern may be a series of parallel lines or a series of orthogonal lines forming a rectangular mesh. The parallel beams may be formed by collimated emitters. Alternatively, they may be formed by means of reflection of an incident beam, from mirrors, prisms, or partially reflective and partially transmissive parallel surfaces.

A method of measuring a dimension of a target site includes the steps of projecting uniformly spaced parallel light beams to form a light pattern having uniformly spaced elements on the target site, aligning the light pattern such that a maximum number of the uniformly spaced elements is positioned along the dimension, and counting the maximum number of the uniformly spaced elements positioned along the dimension. The uniformly spaced elements may be collinear dots or parallel lines. The light pattern may be a series of orthogonal lines forming a rectangular mesh.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
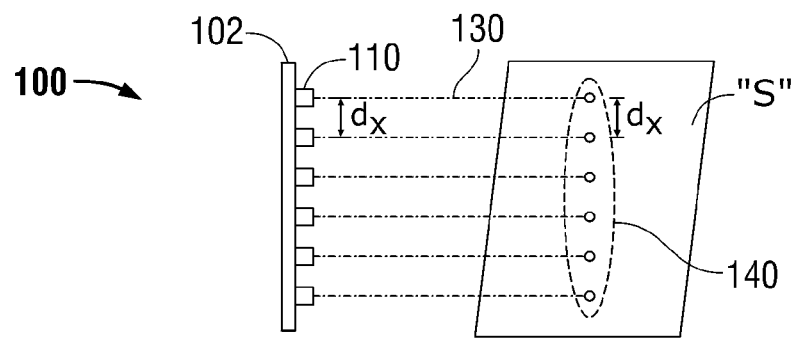
FIG. 1 is a side, schematic view of a metrology system according to the principles of the present disclosure.

Particular embodiments of the present disclosure are described hereinbelow with reference to the accompanying drawings; however, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is farther away from the user. The term "clinician" refers to any medical professional (i.e., doctor, surgeon, nurse, or the like) performing a medical procedure involving the use of embodiments described herein.

As seen in FIG. 1, a metrology system 100 according to an embodiment of the present disclosure is illustrated. Metrology system 100 includes a light row 102 having light emitters 110 attached thereto. Various embodiments of light emitters 110 include LEDs and laser diodes. Each light emitter 110 emits a light beam 130 for creating a light pattern 140 on a target site "S". Light beams 130 are substantially parallel. Adjacent light beams 130 have a substantially uniform distance $d_x$ therebetween. Light beams 130 may be collimated for increased precision of light pattern 140. Light beams 130 may be any suitable form of light, such as coherent, partially coherent, visible, infrared, or ultraviolet. A wavelength of 532 nm may be used to differentiate light beams 130 from a color of any naturally occurring tissue in the human body.

Light pattern 140 may be any pattern suitable for measuring a dimension of target site "S". Light pattern 140 may be a one-dimensional pattern of evenly spaced dots produced by parallel light beams 130. A measurement of the dimension of target site "S" may be determined by counting a number n of even spaced dots appearing on target site "S" and multiplying the number n by the distance $d_x$. As a true size of the dimension is between $nd_x$ and $(n-1)d_x$, a maximum error of either calculation is less than $d_x$. A calculation $(n-½)d_x$ yields a value with a maximum error of $±½d_x$.

Figure 2B:
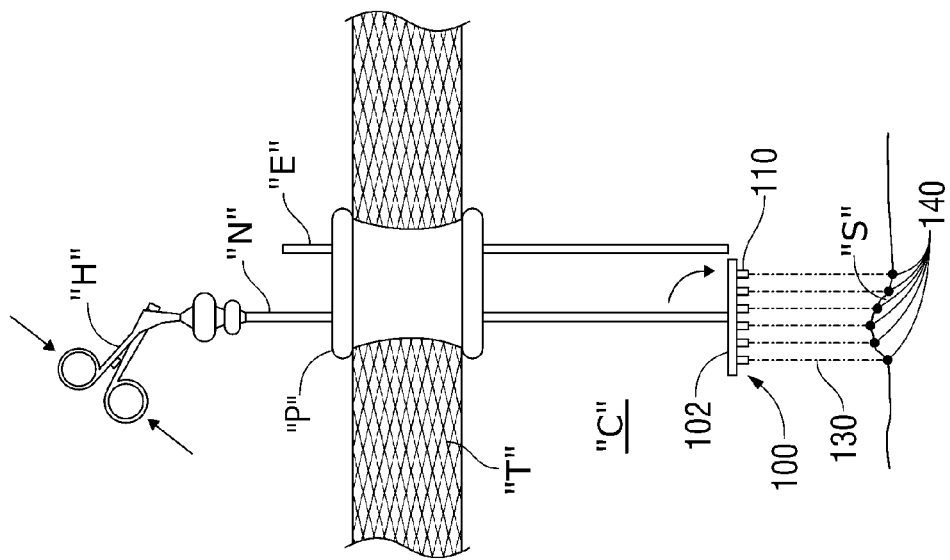
FIGS. 2A-2B are side, schematic views of a method of use of the metrology system of FIG. 1.
Figure 2A:
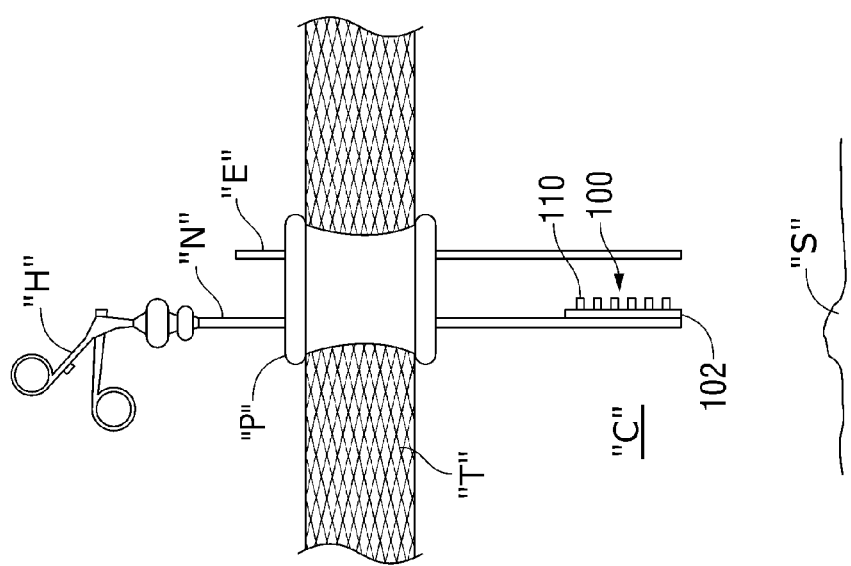

Turning to FIGS. 2A-2B, a method of use of metrology system 100 is illustrated. As seen in FIG. 2A, a target site "S" exists within a cavity "C" under tissue "T". Metrology system 100 is attached to a distal end of a surgical instrument "N" having an actuable handle "H". Surgical instrument "N" is inserted through a surgical access port "P" positioned in an opening in tissue "T". An endoscope "E" is inserted through surgical access port "P" for viewing target site "S". Light row 102 is substantially parallel to surgical instrument "N" during insertion.

As seen in FIG. 2B, light row 102 may be rotated about the distal end of surgical instrument "N", for example, by an actuation of handle "H" of surgical instrument "N" or by manipulation from another surgical instrument. A rotation of light row 102 positions light row 102 parallel to the dimension of target site "S" to be measured. Light emitters 110 emit light beams 130 to create light pattern 140 on target site "S". The number of dots n appearing on target site "S" is visually counted through endoscope "E". Endoscope "E" and/or surgical instrument "N" may be rotated or otherwise positioned to align light pattern 140 such that a maximum number of dots n appears on the dimension of target site "S" to be measured. The dimension may then be calculated using the number of dots n and the distance $d_x$ as described hereinabove.

Figure 3:
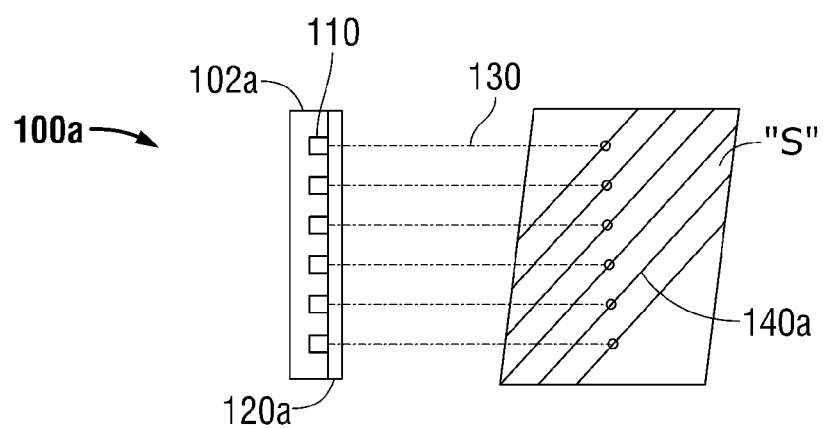
FIG. 3 is a side, schematic view of a metrology system according to another embodiment of the present disclosure.

Turning to FIG. 3, a metrology system in accordance with an alternate embodiment of the present disclosure is generally designated as 100a. Metrology system 100a is similar to metrology system 100 and thus will only be discussed as necessary to identify the differences in construction and operation thereof.

Metrology system 100a has a light row 102a, light emitters 110, and an optical element 120a. Optical element 120a is positioned between light emitters 110 and target site "S". Light emitters 110 are attached to light row 102a. Embodiments of optical element 120a include refractive (lenses) or diffractive (engineered light diffusers) line generating optics. Optical element 120a shapes light beams 130 such that each light beam 130 produces a line on target site "S". A light pattern 140a is produced that includes a line for each light emitter 110, and the lines have a substantially uniform distance $d_x$. A measurement may be taken by counting a number of lines n on target site "S" and applying the calculation described hereinabove for metrology system 100.

Figure 4:
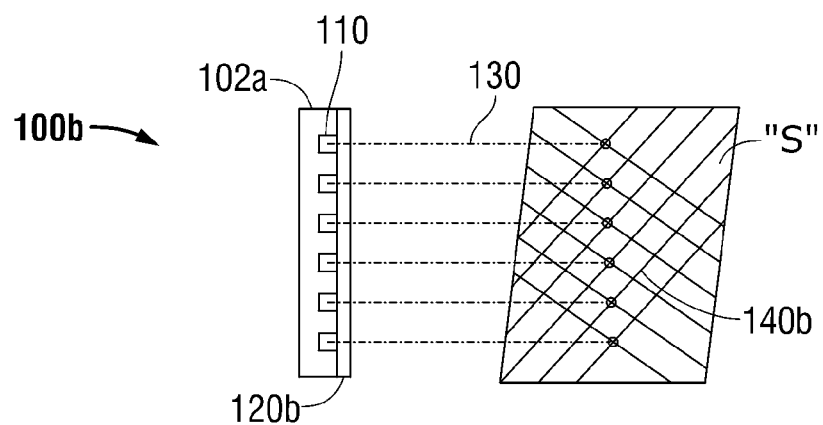
FIG. 4 is a side, schematic view of a metrology system according to another embodiment of the present disclosure.

Turning to FIG. 4, a metrology system in accordance with an alternate embodiment of the present disclosure is generally designated as 100b. Metrology system 100b is similar to metrology system 100a and thus will only be discussed as necessary to identify the differences in construction and operation thereof.

Metrology system 100b includes light row 102a, light emitters 110, and an optical element 120b. An optical element 120b is positioned between light emitters 110 and target site "S". In one embodiment, optical element 120b is a cross generating optical element such as an engineered light diffuser. In another embodiment, optical element 120b is a refractive optical element. Optical element 120b shapes light beams 130 such that each light beam 130 produces two perpendicular intersecting lines on target site "S". A light pattern 140b formed by light beams 130 is a rectangular mesh formed by the intersecting lines. Each line segment between intersection points has a substantially uniform distance $d_x$. A measurement may be taken by counting a number of lines, rectangles, intersections, or a combination thereof on target site "S" and using the distance $d_x$ to calculate a geometric value therefrom.

Figure 5:
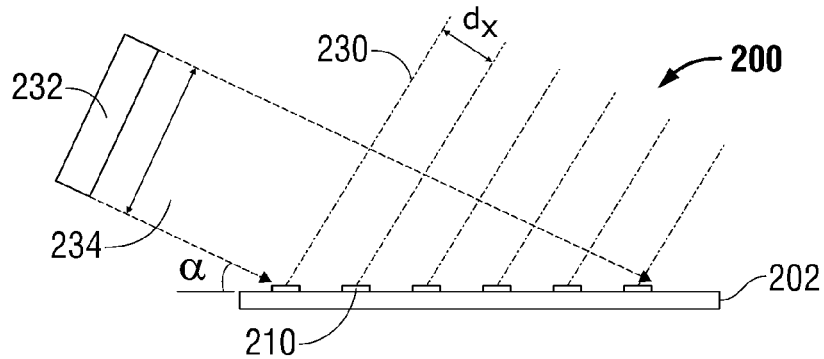
FIG. 5 is a side, schematic view of a metrology system according to another embodiment of the present disclosure.

Turning to FIG. 5, a metrology system in accordance with an alternate embodiment of the present disclosure is generally designated as 200. Metrology system 200 is similar to metrology system 100 and thus will only be discussed as necessary to identify the differences in construction and operation thereof.

Metrology system 200 includes a light row 202 having reflectors 210 attached thereto. Reflectors 210 are evenly spaced. Embodiments of reflectors 210 include mirrors and prisms. An incidental beam projector 232 projects an incidental beam 234 onto reflectors 210 at an angle α. Incidental beam projector 232 may be attached to light row 202. Alternatively, incidental beam projector may be a component of a separate device. Incidental beam 234 is sufficiently wide to be projected onto a number of reflectors 210 necessary for measurement of a dimension of a target site. Reflectors 210 reflect incidental beam 234 as light beams 230 having a substantially uniform distance $d_x$ therebetween. Incidental beam 234 is collimated to produce light beams 230 that are substantially parallel.

Figure 6:
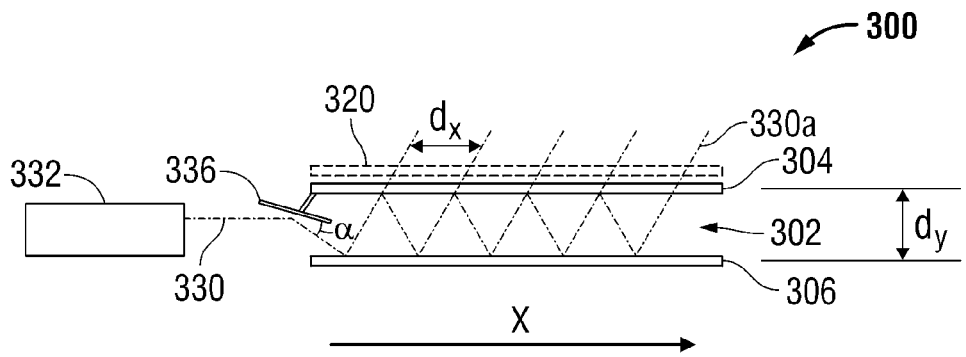
FIG. 6 is a side, schematic view of a metrology system according to another embodiment of the present disclosure.

Turning to FIG. 6, a metrology system in accordance with an alternate embodiment of the present disclosure is generally designated as 300. Metrology system 300 is similar to metrology system 200 and thus will only be discussed as necessary to identify the differences in construction and operation thereof.

As seen in FIG. 6, metrology system 300 has a light row 302 including two parallel surfaces 304, 306 a distance $d_y$ apart. Metrology system 300 may further include a line or cross generating optical element 320 between surface 304 and a target site. Surface 304 is partially reflective and partially transmissive. Surface 306 is at least partially reflective. A light source 332 projects a light beam 330 in a direction X toward a space between surface 304 and surface 306. A reflector 336 reflects light beam 330 toward surface 306 at an angle α. Light beam 330 is propagated along light row 302 having multiple reflections between surfaces 304, 306. Incidence of light beam 330 upon surface 304 causes transmitted beams 330a to be transmitted through surface 304 toward the target site. Transmitted beams 330a are substantially parallel and have substantially uniform distance $d_x$ therebetween. Angle α distance $d_y$ may be varied to alter distance $d_x$. Transmittance of surface 304 may be configured or adjusted to compensate for decreasing brightness of light beam 330 along direction X.

Figure 7:
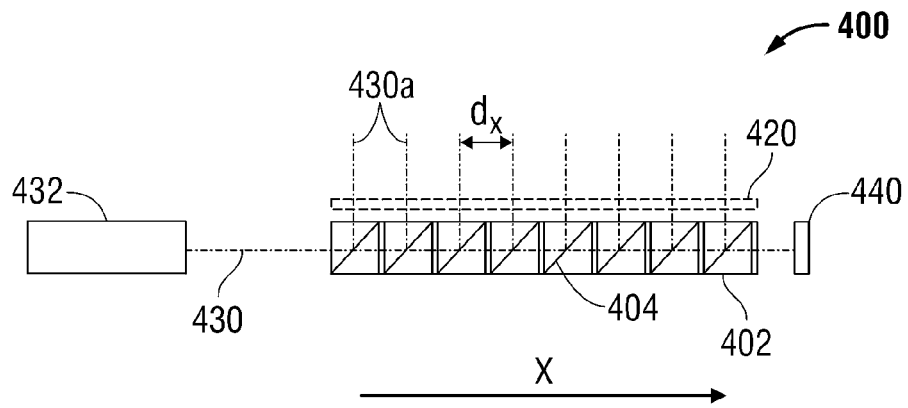
FIG. 7 is a side, schematic view of a metrology system according to another embodiment of the present disclosure.

Turning to FIG. 7, a metrology system in accordance with an alternate embodiment of the present disclosure is generally designated as 400. Metrology system 400 is similar to metrology system 300 and thus will only be discussed as necessary to identify the differences in construction and operation thereof.

As seen in FIG. 7, metrology system 400 includes a light row 402 having beam splitters 404 therein. Beam splitters 404 are partially transmissive and partially reflective. Embodiments of beam splitters 404 include cubic beam splitters and thin partially reflective plates. Metrology system 400 further includes a light source 432 for projecting a light beam 430 in a direction X sequentially through beam splitters 404. Upon incidence of light beam 430 with a beam splitter 404, a reflected beam 430a is reflected by the beam splitter 404 toward a target site. Reflected beams 430a are substantially parallel and have a substantially uniform distance $d_x$ therebetween. A transmitted portion of light beam 430 continues to travel in direction X. Each beam splitter 404 may have a different splitting ratio to compensate for changes in brightness of light beam 430 as light beam 430 is propagated in direction X. Metrology system 400 may include a line or cross generating optical element 420 between beam splitters 404 and a target site. Metrology system 400 may further include a beam stop 440 to block light beam 430 from propagating further along direction X.

Methods of use of metrology systems 100a, 100b, 200, 300, and 400 are substantially identical to the method of use of metrology system 100 described hereinabove.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. A surgical instrument including a metrology system comprising:
    an elongate shaft; and
    a collinear array of uniformly spaced light elements for propagating parallel light beams, the collinear array of uniformly spaced light elements rotatable coupled to a distal end of the elongate shaft, wherein the parallel light beams assist in producing a light pattern dimensioned to encompass a target site, the light pattern having a plurality of uniformly spaced markings for determining dimensions of the target site by counting a number of the plurality of uniformly spaced markings encompassing the target site.

2. The surgical instrument as in claim 1, wherein the collinear array of uniformly spaced light elements are attached to an endoscope.

3. The surgical instrument as in claim 1, wherein the light pattern comprises uniformly spaced collinear dots.

4. The surgical instrument as in claim 1, further comprising a light pattern generating optical element for producing a two-dimensional light pattern from the parallel light beams.

5. The surgical instrument as in claim 4, wherein the two-dimensional light pattern is a series of parallel lines.

6. The surgical instrument as in claim 4, wherein the two-dimensional light pattern is a series of orthogonal lines forming a rectangular mesh.

7. The surgical instrument as in claim 4, wherein the light pattern generating optical element is diffractive.

8. The metrology system surgical instrument as in claim 4, wherein the light pattern generating optical element is refractive.

9. The surgical instrument as in claim 1, wherein the collinear array of uniformly spaced light elements are collimated emitters.

10. The surgical instrument as in claim 1, wherein the collinear array of uniformly spaced light elements reflect an incident beam.

11. The surgical instrument as in claim 10, wherein the collinear array of uniformly spaced light elements are mirrors.

12. The surgical instrument as in claim 10, wherein the collinear array of uniformly spaced light elements are prisms.

13. The surgical instrument as in claim 10, wherein the collinear array of uniformly spaced light elements include partially reflective and partially transmissive parallel surfaces.

14. A method of measuring a dimension of a target site, comprising:
    providing a surgical instrument including an elongate member and a light row having light emitters, the light row coupled to a distal end of the elongate member;
    positioning the light row in alignment with the elongate member;
    inserting the light row through an opening in tissue;
    rotating the light row about the distal end of the elongate member such that the light row is parallel to the target site;
    projecting uniformly spaced parallel light beams to form a light pattern having uniformly spaced elements on the target site;
    aligning the light pattern such that a maximum number of the uniformly spaced elements is positioned on the target site; and
    counting the maximum number of the uniformly spaced elements encompassing the target site.

15. The method as in claim 14, wherein projecting uniformly spaced parallel light beams includes projecting collinear dots.

16. The method as in claim 14, wherein projecting uniformly spaced parallel light beams includes projecting parallel lines.

17. The method as in claim 14, wherein aligning the light pattern includes aligning the light pattern including orthogonal lines forming a rectangular mesh on the target site.

* * * * *